United States Patent
Paradis

(10) Patent No.: US 6,692,478 B1
(45) Date of Patent: Feb. 17, 2004

(54) SWABBABLE NEEDLELESS VIAL ACCESS

(76) Inventor: Joseph R. Paradis, P.O. Box 22238, Hilton Head Island, SC (US) 29925

( * ) Notice: Subject to any disclaimer, the term of this patent is extended or adjusted under 35 U.S.C. 154(b) by 756 days.

(21) Appl. No.: 09/073,022

(22) Filed: May 4, 1998

(51) Int. Cl.⁷ .................................................. A61B 19/00
(52) U.S. Cl. ........................ 604/403; 604/411; 604/415; 604/249; 604/905
(58) Field of Search .......................... 604/82, 246, 247, 604/249, 403, 411, 414, 415, 416, 905, 533, 536, 537; 215/247, 249, 250, 274, 277, DIG. 3; 251/149.1–149.4; 147/27, 98, 319, 329, 366

(56) References Cited

U.S. PATENT DOCUMENTS

| | | | | | |
|---|---|---|---|---|---|
| 5,332,113 A | * | 7/1994 | Kusler, III et al. | ......... | 215/249 |
| 5,429,256 A | * | 7/1995 | Kestenbaum | ................ | 215/247 |
| 5,569,235 A | * | 10/1996 | Ross et al. | ................... | 604/403 |
| 5,620,434 A | * | 4/1997 | Brony | ......................... | 604/406 |
| 5,895,383 A | * | 4/1999 | Niedospial, Jr. | ............. | 604/403 |
| 5,902,298 A | * | 5/1999 | Niedospial, Jr. et al. | .... | 604/414 |
| 5,921,419 A | * | 7/1999 | Niedospial, Jr. et al. | .... | 215/247 |

* cited by examiner

Primary Examiner—Weilun Lo
(74) Attorney, Agent, or Firm—G. Kersey

(57) ABSTRACT

A method of sterile needless vial access, utilized to transfer materials from one unit to another. The method utilizes a swab-able access port and a blunt cannula. The access port receives the blunt cannula to couple and aseptically transfer medical and body fluids. The swab-able access port permits disinfectant treatment before receipt of the blunt cannula to limit and prevent contamination of sterile fluids.

19 Claims, 10 Drawing Sheets

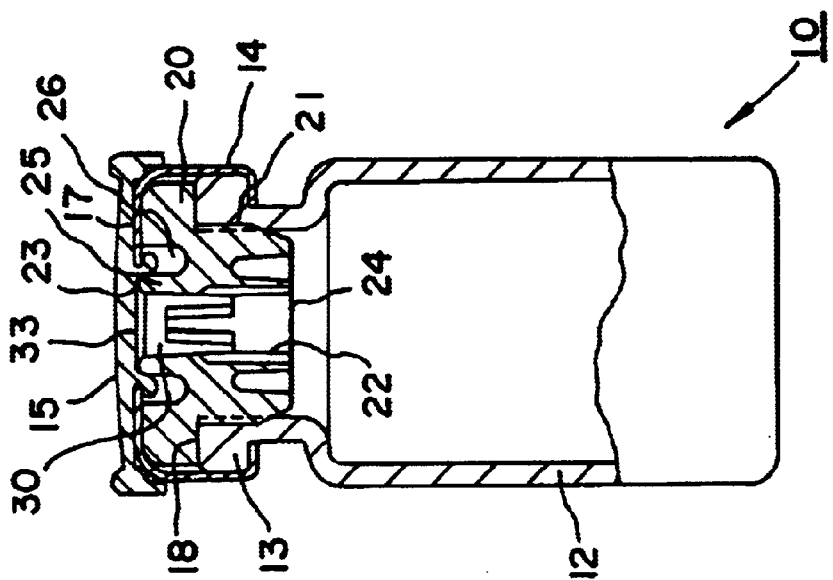
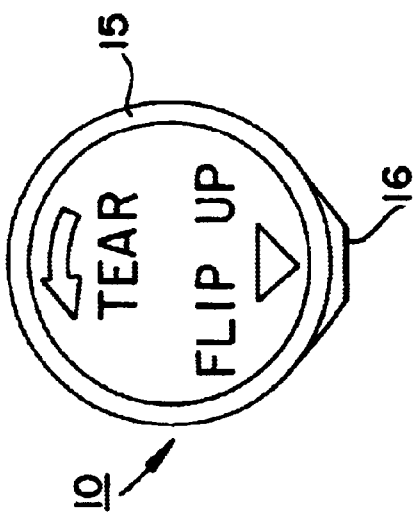
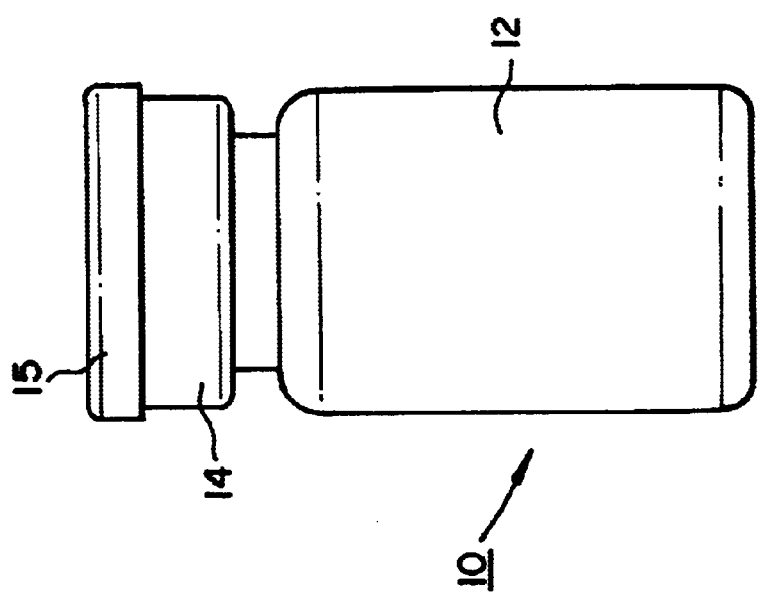

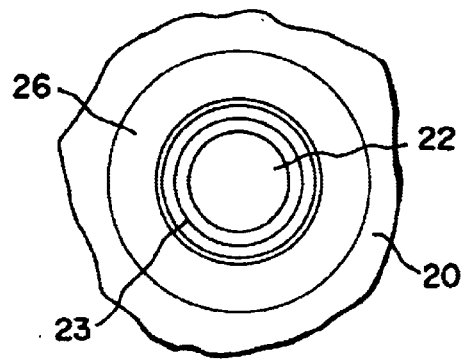
Fig. 2F
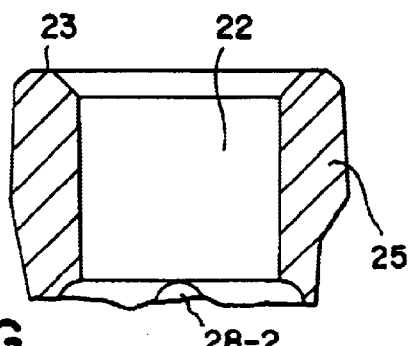
Fig. 2D
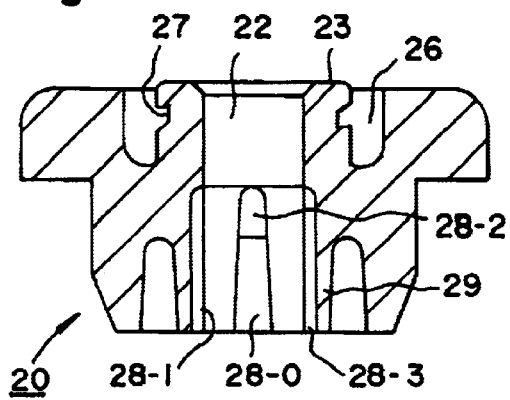
Fig. 2G
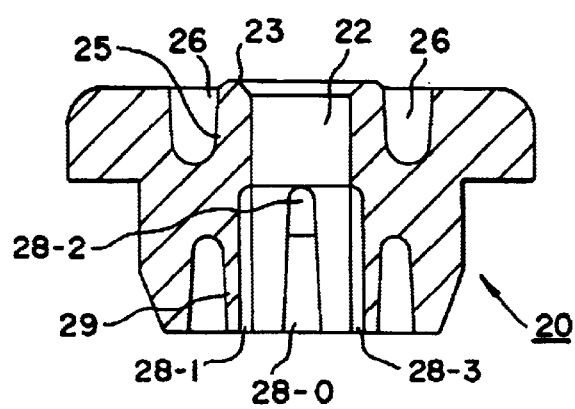
Fig. 2C
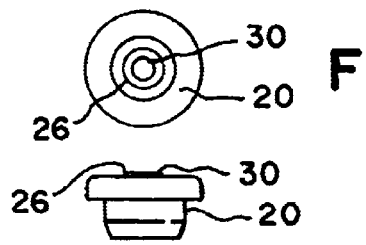
Fig. 2B
Fig. 2A
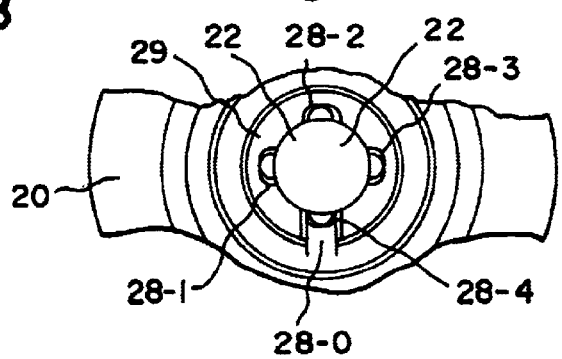
Fig. 2E

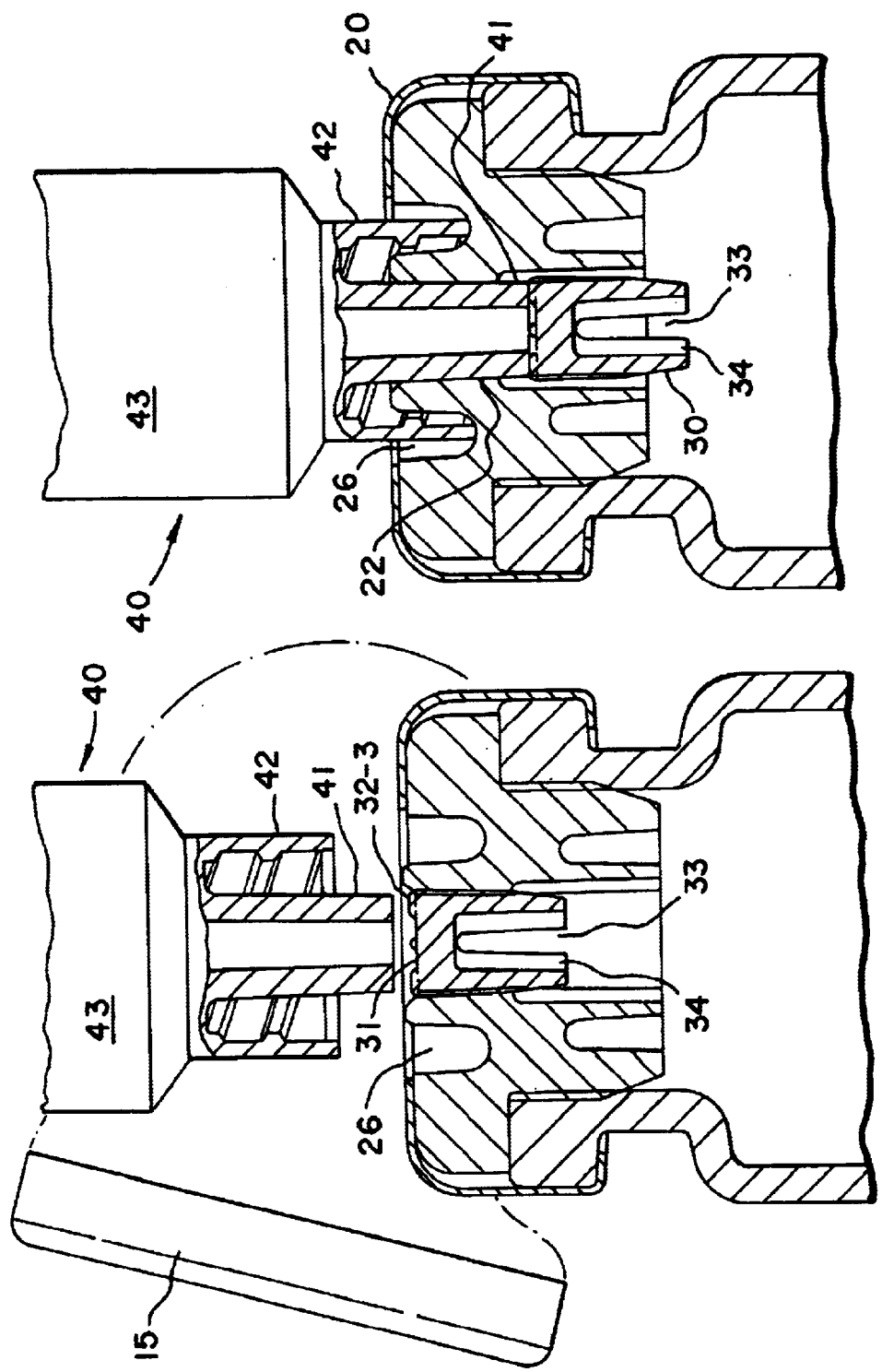

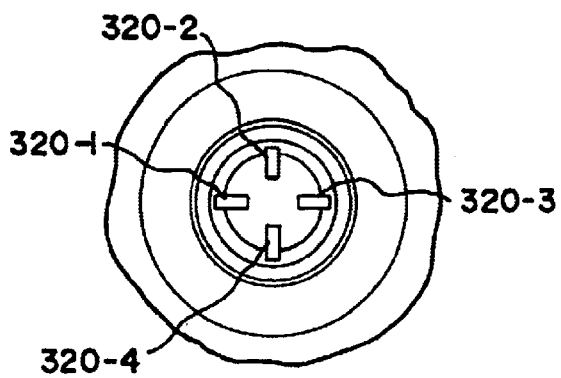
Fig. 6F
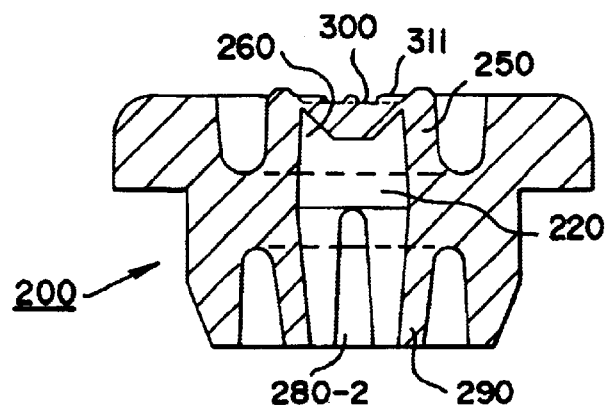
Fig. 6D
Fig. 6B
Fig. 6C
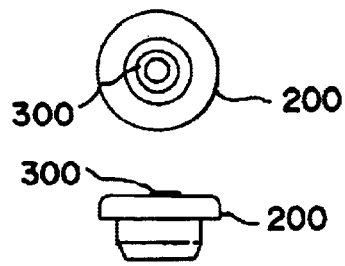
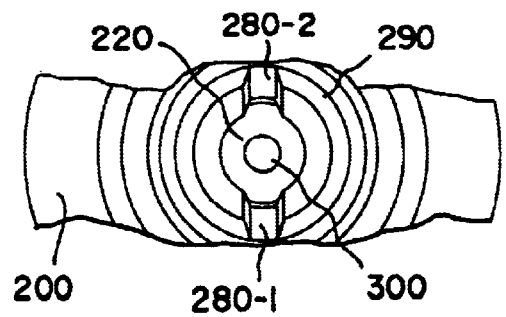
Fig. 6A
Fig. 6E

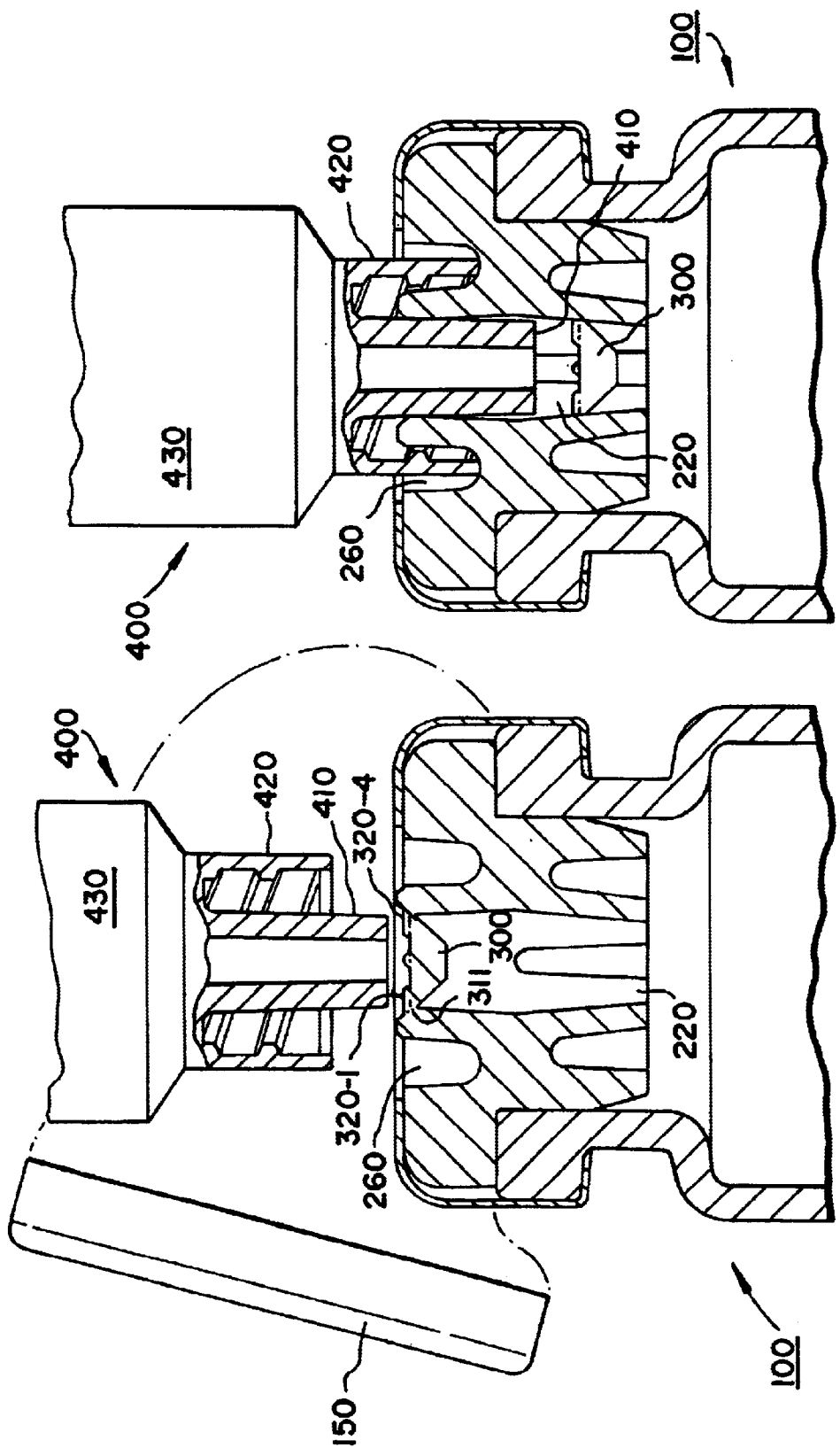

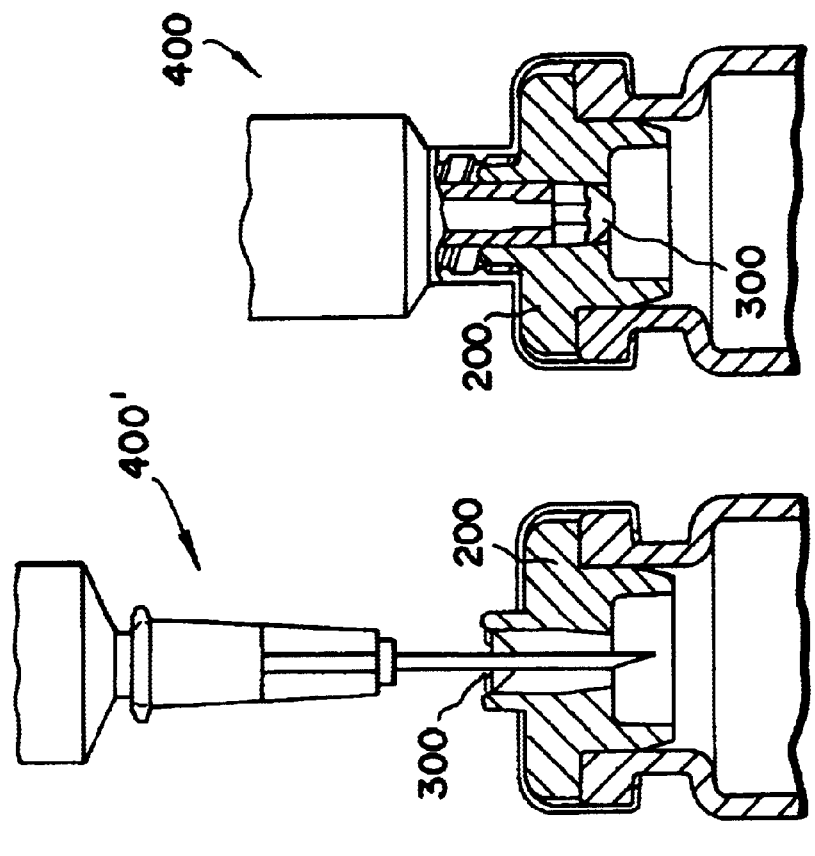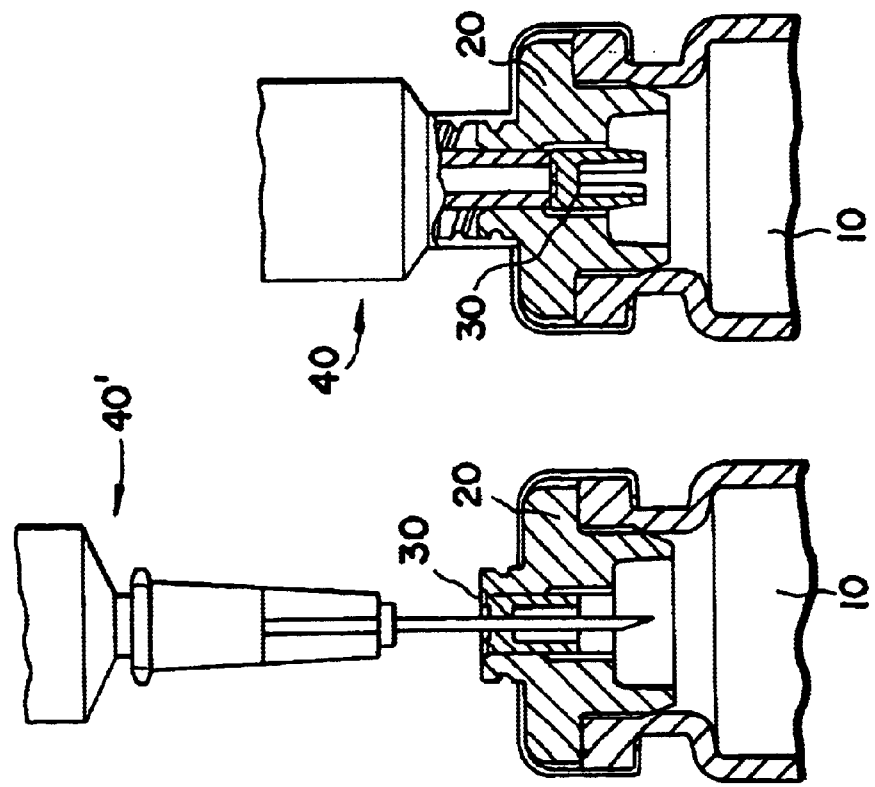

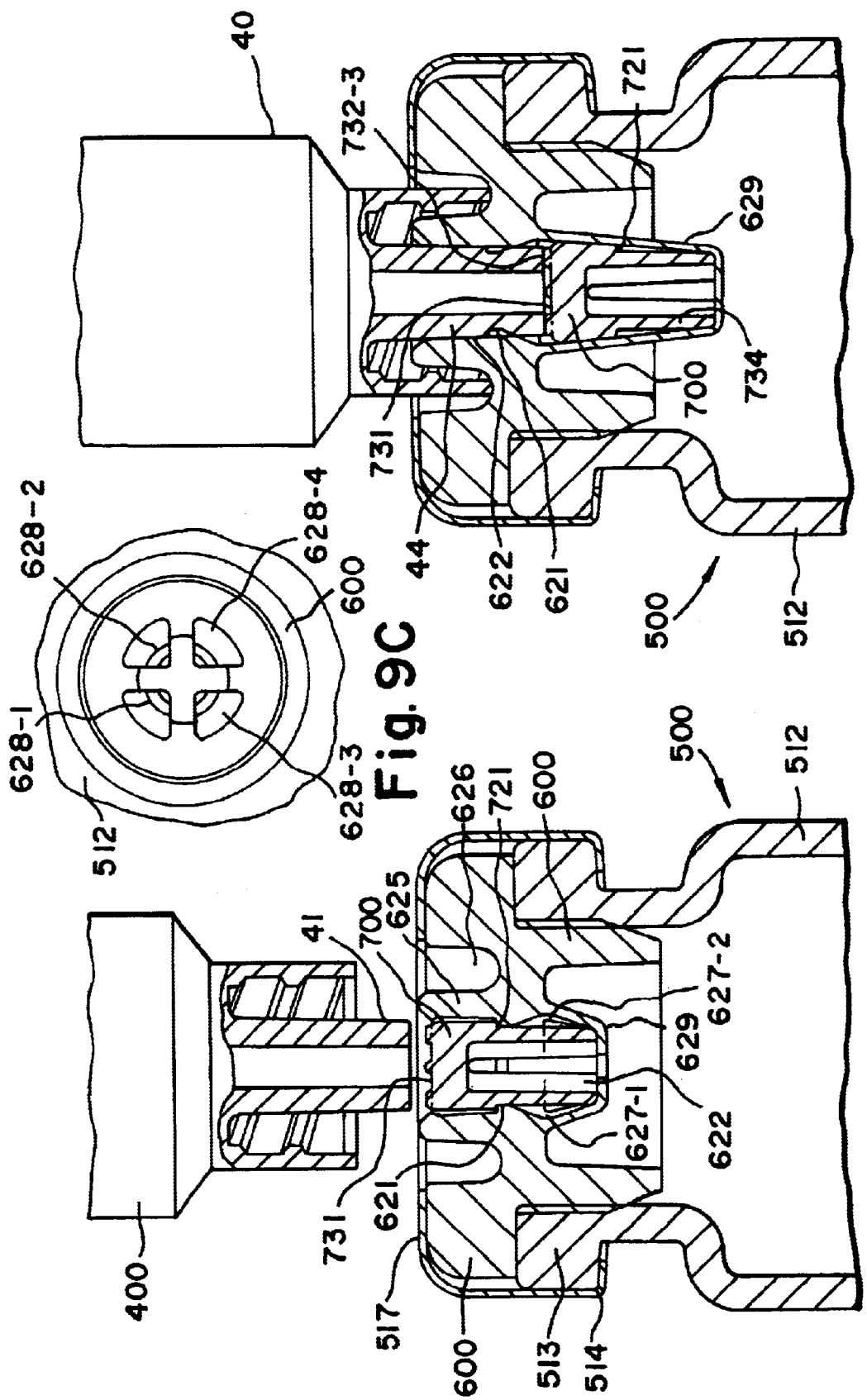

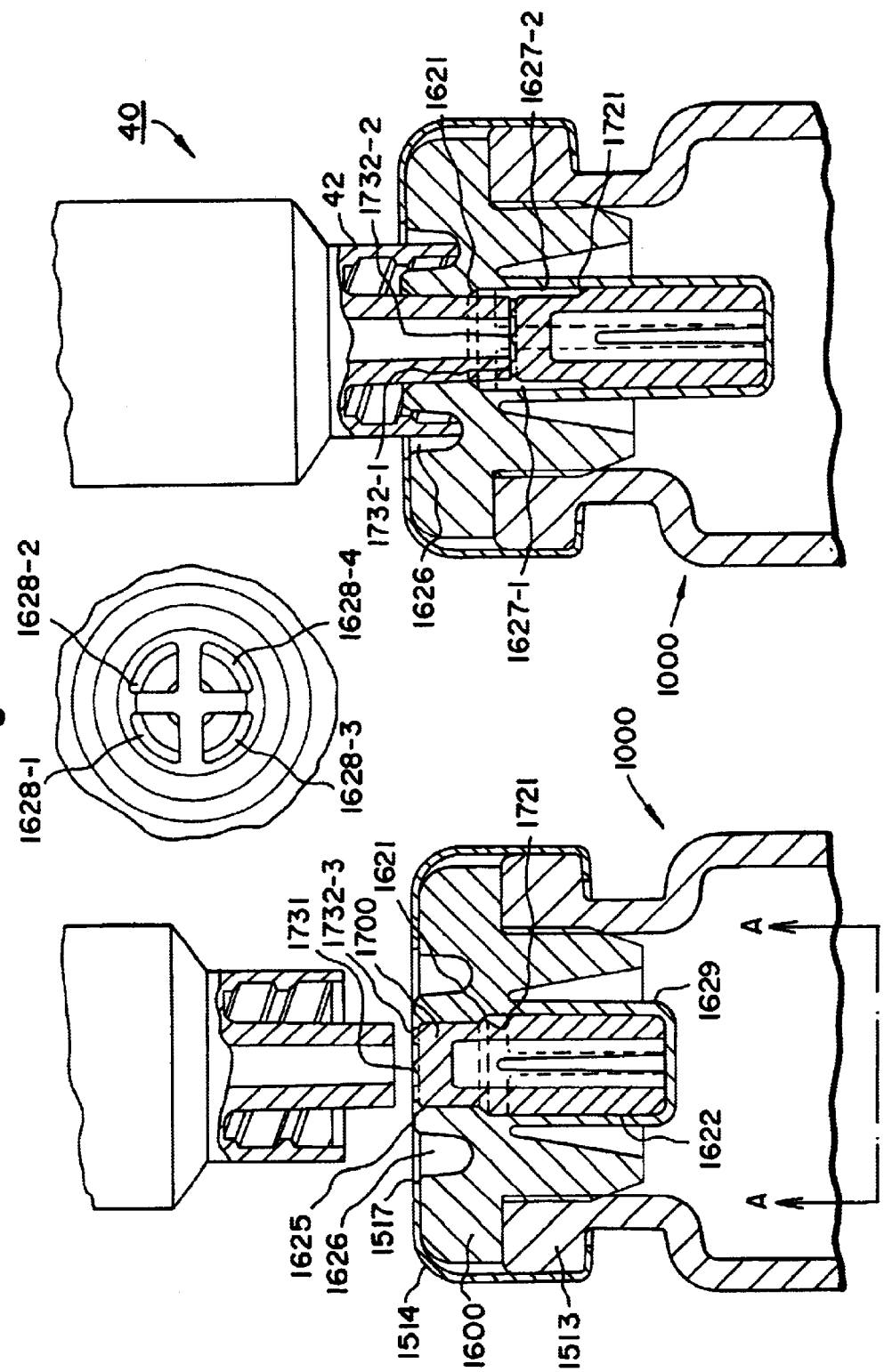

SWABBABLE NEEDLELESS VIAL ACCESS

FIELD OF THE INVENTION

This invention relates to coupling systems for one transfer of materials from one unit to another, and, more particularly, to coupling units with a first unit including a a swabbable access port and a second unit including a blunt cannula. The access port receives the blunt cannula to effect a coupling of particular medicinal applicability for medications and body fluids. The swabbability of the access port allows disinfectant treatment before receipt of the blunt cannula to limit the extent to which pathogens can enter the cannula after coupling is effected.

BACKGROUND OF THE INVENTION

In medical practice, containers for medication typically are bottles capped with rubber-like stoppers. A tamper-evident seal surrounds the stopper and at least the upper portion of the container. To administer medication, the seal is removed, a syringe with a needle or cannula is used to puncture the rubber stopper and withdraw a proper dosage for aministration to a patient.

The need for a needle or cannula presents a potential hazard, both to medical personnel and to the patient. There is significant risk of infection by blood-transmitted diseases, AIDS and hepatitis from needle sticks.

Accordingly, it is an object of the invention to reduce the hazards associated with the administration of medication. A related object is to reduce the hazards associated with removal of medication from sealed containers.

In additional to medicinal containers, pointed needles or annulae have been widely used in conjuction with other forms of access ports, which take the form of a septum or piercable membrane. An illustrative access port that is used with a piercing cannula is disclosed in Zdeb U.S. Pat. No. 4,412,573 "Injection Site" assigned to Baxter International Inc. of Deerfield, Ill.

The pointed cannula can be forced through the septum in order to establish fluid communication between the cannula and the container housing a medicinal substance. Access ports that are pierced by a cannula can be physically damaged by repetitive piercings and produce coring or laceration of the access port, which can result in leakage.

For standard drug vials, the access ports take the form of rubber stoppers which are routinely entered using conventional hypodermic needles. In order to maintain sterility, the stopper is swabbed with a disinfectant before there is a needle entry. After repeated entries, the stopper can leak because of coring and no longer function as a swabbable sterile barrier.

In addition to pathogens which may become present in the pierced sites, particulate matter can be generated and injected into a patient, along with pathogens. Alternatively, the pathogens and particulate matter may contaminate the contents of the vial. These conditions are pronounced with vials that are accessed multiple times.

Moreover, pointed cannulae used with drug vials pose a health risk to their users because of problems associated with infectious agents. Despite the fact that personnel using pointed cannulae do so with great care, from time to time accidents occur, and the users are jabbed or suffer needle sticks.

In an attempt to overcome difficulties associated with the use of pointed cannulae, "dispensing pins" can be used to penetrate the site or stopper of multiple dose vials. A dispensing pin typically takes the shape of a sharp spike and can be used with a check valve to limit fluid leakage. One end of the spike has standard luer fitment that is typically closed off, when not in use, by a cap. Dispensing pins tend to disengage from the vial stopper with resultant leakage. Further, it is difficult to maintain sterile conditions on this kind of multiple dose system.

One attempted solution has been to eliminate sharp cannulae and use blunt cannulae instead. An example is Garrett et al. U.S. Pat. No. 4,197,848 "Closed Urinary Irrigation Site", assigned to Baxter International. In Garrett the injection site is a relatively low pressure device with a relatively thin, molded sealing member that has an opening which permits a blunt cannula to be forced through the sealing member into fluid communication with the interior of the injection site.

Injection sites used with a blunt cannula have the advantage that the cannula will not pierce the skin of a user, but the pre-slit injection site has to reseal with enough force that fluids do not ooze outwardly and not allow airborne particulate matter, bacterial or viral, to enter.

Hence, there continues to be a need for an injection site which can be used with a variety of solutions and over a range of fluid pressures. Further, there continues to be a need for such an injection site which will reliably reseal even after many insertions of a blunt cannula.

If intended to be reusable, the injection site should be able to receive a large number of insertions of the cannula without displaying reseal failure. Such an injection site should provide for alignment of the cannula on insertion to result in less chance of damage to the injection site after repeated insertions. In addition, although pointed cannulae desirably are to be avoided, in some situations they may be the only ones available, so that the injection site also should be usable with pointed cannulae.

Further, the injection site should be usable with a blunt cannula with a reasonable level of insertion force that will permit health care personnel to readily insert the cannula, but yet not have the cannula easily displaced after insertion.

One attempt to meet these objectives is disclosed in Dudar et al. U.S. Ser. No. 425,790 (Oct. 23,1989) "Pre-Slit Injection Site" in which one end of a housing carries a pre-slit septum, and a second end has a coupling to adapt the housing to standard vials. The coupling or a vial adapter includes a spike with openings that allow drainage of fluid in the vial through the spike and into the injection site. The vial adapter has a skirt which protects the adapter spike in both manufacture and use. The skirt also permit locking engagement of the adapter with injection site to standard vials, despite dimensional variations in vial closures. The coupling spike can having a barb that can be inserted into a standard vial and resist disengagement. A blunt cannula is used with the combination of the injection site with the coupling. This system is both complex and cumbersome.

Accordingly it is a further object of the invention to achieve the foregoing advantages without the need for a pre-slit injection site.

SUMMARY OF THE INVENTION

In accomplishing the foregoing and related objectives, the invention provides for a swabbable access port formed by a stopper having a bore extending from an entry position to an exit position; and a swabbable plug in the bore at the entry position and movable in the bore.

In accordance with one aspect of the invention the swabbable plug extends integrally across the bore and can be frangibly connected to the bore, or be slidably connected to the bore.

In accordance with another aspect of the invention the swabbable plug has a non-planar external surface and is pierceable by a cannula. The stopper can have a collar at the entry position, and the collar can have external Luer threads.

A stretchable and apertured membrane can span the exit position of the bore so that when the plug is depressed into the bore by, for example, the end of a fitment, the plug can be restored to its original, swabbable position at the entry position of the stopper when the fitment is removed.

In accordance with a method of the invention for accessing a port, the steps include (a) swabbing a movable plug positioned in the bore of a stopper, for which the bore extends from an entry position, where the plug is swabbed, to an exit position; and (b) moving the plug within the bore away from the entry position; whereby communication can be established along the bore between the entry position and the exit position.

The method further includes the step of swabbing an integral surface of the movable plug, with the surface extending integrally across the bore. The swabbing can take place with respect to frangible connections to the bore.

In one aspect of the method, further steps include slidably moving the plug along the bore; engaging the plug by a fitment with a transverse gap between a portion of the exterior surface of the plug and the engagement end of the fitment; and piercing the plug by a cannula.

In another aspect of the method the steps include engaging a collar of the stopper at the entry position of the bore; engaging external Luer threads of the collar; sretching an apertured membrane that spans the exit position of the bore; and causing fluid to flow in an auxiliary channel of the bore when the plug is depressed in the bore.

A system of the invention for the transfer of medication from a container includes (a) a needleless syringe having a blunt tubular end; (b) a stopper positioned in a neck portion of the container and having a central throughbore extending from an outer surface of the stopper to the interior of the container; (c) a plug extending into the bore from the outer surface of the stopper; (d) protrusions on the plug for engagement by the end of the syringe permitting fluid flow between the syringe and the plug; and (e) an auxiliary channel in the bore permitting the fluid flow to extend between the container and the syringe.

The invention enables the needleless and disinfected transfer of medication using a stopper with a movable plug having an integral surface for engagement of the plug by a fitment, such as the Luer end of a syringe. By using the invention, medication can be withdrawn from a container with or without the use of a needle, after disinfectant treatment of the engagement surface of the plug to remove pathogens and possible contaminants.

BRIEF DESCRIPTION OF THE DRAWINGS

Various other features, advantages and characteristics of the invention will become apparent after considering several illustrative embodiments, taken in conjunction with the drawings, in which:

FIG. 1A is a plan view of a stoppered medicinal container in accordance with the invention;

FIG. 1B is a top view of the stoppered medicinal container of FIG. 1A;

FIG. 1C is a partial sectional view of the stoppered medicinal container of FIG. 1A;

FIG. 2A is a full-scale side view of the stopper and plug of the medicinal container of FIG. 1A;

FIG. 2B is a full-scale top view of the stopper and plug of the medicinal container of FIG. 1A;

FIG. 2C is an enlarged sectional view of the stopper of the medicinal container of FIG. 1A;

FIG. 2D is a partial top view of the stopper of FIG. 2C;

FIG. 2E is a partial bottom view of the stopper of FIG. 2C;

FIG. 2F is an enlarged, partial sectional view of an alternative stopper collar portion of the invention;

FIG. 2G is an enlarged sectional view of an alternative stopper for the container of FIG. 1C;

FIG. 3B is a full-scale top view of the plug of the stopper of FIG. 2A;

FIG. 4A is an enlarged, partial sectional view of the container of FIG. 1C preparatory to activation by a Luer fitment;

FIG. 4B is an enlarged, partial sectional view of the container of FIG. 1C during activation by a Luer fitment;

FIG. 6A is a full-scale side view of the stopper and plug of the medicinal container of FIG. 5A;

FIG. 6B is a full-scale top view of the stopper and plug of the medicinal container of FIG. 5A;

FIG. 6C is an enlarged sectional view of the stopper and plug of the medicinal container of FIG. 5A;

FIG. 6D is a partial top view of the stopper and plug of FIG. 6C;

FIG. 6E is a partial bottom view of the stopper of FIG. 6C;

FIG. 6F is an enlarged, partial sectional view showing the alternative stopper for the container of FIG. 5C;

FIG. 7A is an enlarged, partial sectional view of the container of FIG. 5C preparatory to activation by a Luer fitment;

FIG. 7B is an enlarged, partial sectional view of the container of FIG. 5C during activation by a Luer fitment;

FIG. 8A is a partial sectional view of the container of FIG. 1C during activation by a cannula;

FIG. 8B is a partial sectional view of the container of FIG. 1C during activation by a Luer fitment;

FIG. 8C is a partial sectional view of the container of FIG. 5C during activation by a cannula;

FIG. 8D is a partial sectional view of the container of FIG. 5C during activation by a Luer fitment;

FIG. 9A is an enlarged, partial sectional view of another alternative embodiment of the invention preparatory to activation by a Luer fitment;

FIG. 9B is an enlarged, partial sectional view of another alternative embodiment of the invention during activation by a Luer fitment;

FIG. 9C is a partial sectional view of the bottom of the stopper and plug combination of FIGS. 9A and 9B;

FIG. 10A is an enlarged, partial sectional view of still another alternative embodiment of the invention preparatory to activation by a Luer fitment;

FIG. 10B is an enlarged, partial sectional view of another alternative embodiment of the invention during activation by a Luer fitment; and FIG. 10C is a partial sectional view of the bottom of the stopper and plug combination of FIG. 10A.

DETAILED DESCRIPTION

Figure 3D:
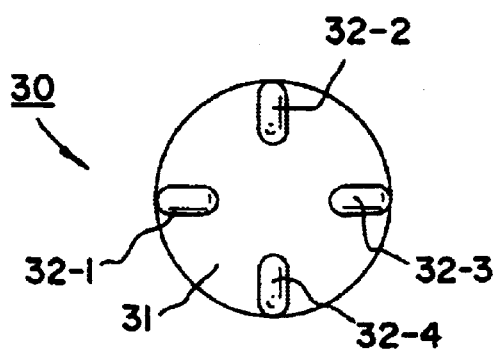
FIG. 3D is an enlarged view of the plug of FIG. 3B.

As shown in the Figures, there are three basic components for the needleless transfer of medication between a container 10 and a syringe. Besides the syringe, which may be needleless, the invention makes use of a stopper 20 and a plug 30 in the stopper 20.

The syringe, such as the syringe 40 of FIG. 4A, may be of any commercially available type, including the Luer-lock type shown in the Figures.

It is the combination of the stopper 20 and the plug 30 that permits the needleless transfer of medication with reduced danger of pathogen and other contamination.

As shown in FIG. 1A, the medicinal container 10 includes a bottle 12 with a top mouth portion 13 encircled by a flange 14 and sealed by a cover 15 that is instructed in FIG. 1B to be "flipped up" at a corner 16 and torn to expose the flange rim 17 of FIG. 1C, which shows the stopper 20 in snug fit within mouth portion 13 of the bottle 12. The stopper 20 may include a rib 21, or the like, to improve the seal. The flange 14 overlies the top edge 18 of bottle 12.

The stopper 20 may be of an elastomeric, rubber-like material or a hard, self-lubricating plastic such as TEFLON M material. The stopper 20 has a throughbore 22 which extends from an entry portion 23 to an exit portion or opening 24.

Aligned with the entry portion 23 of the stopper 20 is the outer surface 33 of the plug 30. Surrounding the plug 30 is a neck 25 of the stopper 20. In FIG. 1C the neck 25 is surrounded by a recess 26 below the entry position 23. As indicated in FIG. 2F, the neck 24 can have Leur threads 27 in the recess 26.

As more clearly shown in FIGS. 2C and 2E, the bore 22 of the stopper 20 has side channels 28-1 through 28-4, with the channel 26-2 having a bottom opening 28-0 in the side wall 29, as shown in FIG. 2D.

Figure 3C:
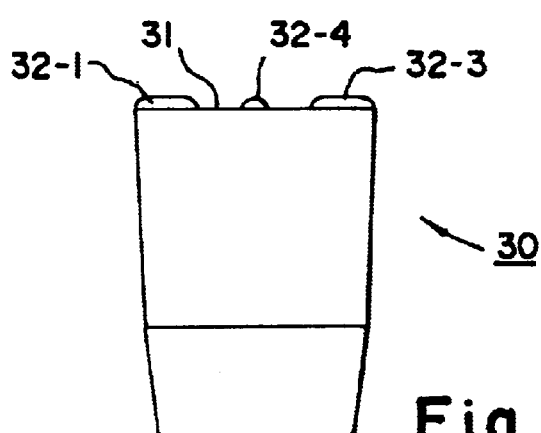
FIG. 3C is an enlarged view of the plug of FIG. 3A.
Figure 3A:
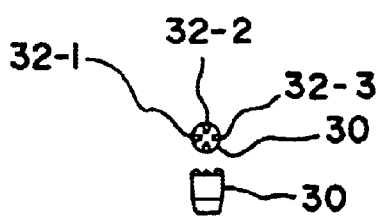
FIG. 3A is a full-scale side view of the plug of the stopper of FIG. 2A.
Figure 3E:
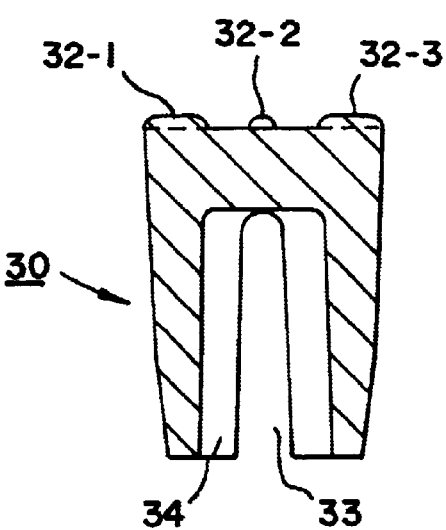
FIG. 3E is a sectional view of the plug of FIG. 3C.
Figure 3F:
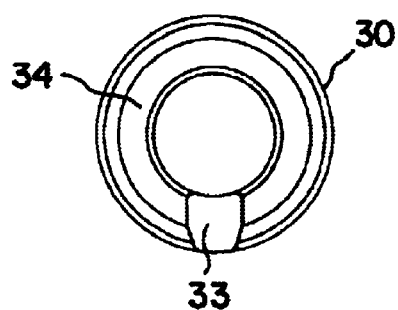
FIG. 3F is a bottom view of the plug of FIG. 3E.

Details of the plug .30 are shown in FIGS. 3C though 3F. The plug 30 has an upper surface 31 with protrusions 32-1 though 32-4 in order to space the tip of an inserted fitment, as discussed below, from the surface 31 in order to allow fluid flow from the fitment to the surface 31. The plug 30 also has longitudinal groove 33 in the side wall 34.

As shown in FIG. 4A, which is an enlarged, partial sectional view of the container of FIG. 1C, after removal of the cap 15, a Luer fitment in the form of a syringe 40 has its tip 41 brought near the surface 31 of the plug 30, preparatory to activation. The syringe 40 has its blunt tubular leading end tip 41 surrounded by a Luer threaded housing 42, includes a plunger (not shown) and is calibrated with indicia which permit a proper dosage of medication to be withdrawn into the barrel 43 of the syringe 40.

As indicated in FIG. 4B, when the tip 41 is brought into contact with the protuberances 32-1 through 32-4, and the housing 42 is pushed into the groove 26, the plug 30 is depressed into the bore 22 and fluid can be exchanged between the container and the syringe. The flow is through the channels and the bore of the syringe.

In actual practice, blunt end 41 is inserted against the plug 30 and into the bore 21 with the plunger extended. For the withdrawal of fluid, air is injected into the container 10 to pressurize contained fluid and facilitate its withdrawal. The plunger can be drawn out of the barrel 43 of the syringe 40 to the position appropriate for a desired dosage. There is an interference fit between blunt nose end 44 and the bore 22 to effectively grip the syringe in the stopper during medication transfer to minimize spillage.

Figure 5B:
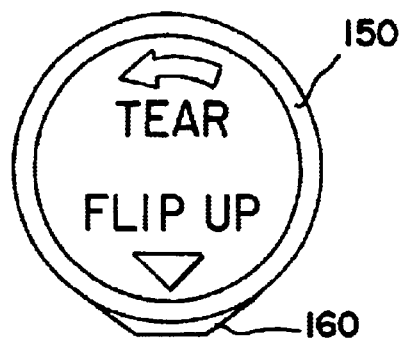
FIG. 5B is a top view of the stoppered medicinal container of FIG. 5A.
Figure 5A:
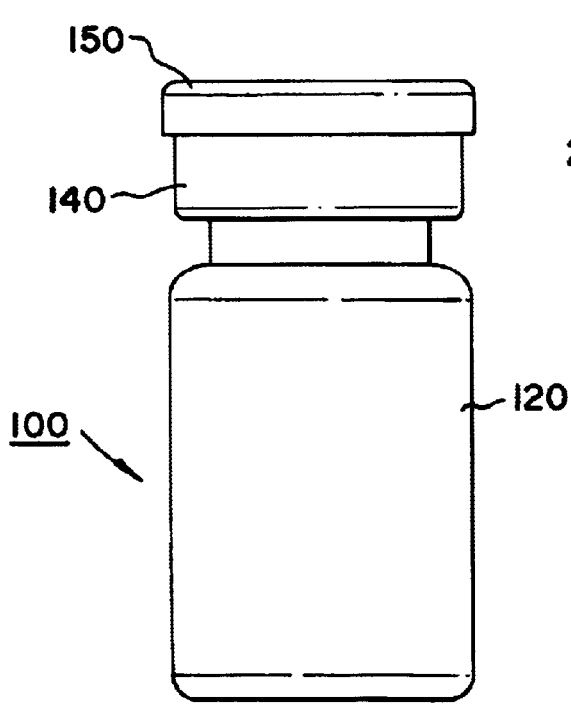
FIG. 5A is a plan view of an alternative, stoppered medicinal container in accordance with the invention.
Figure 5C:
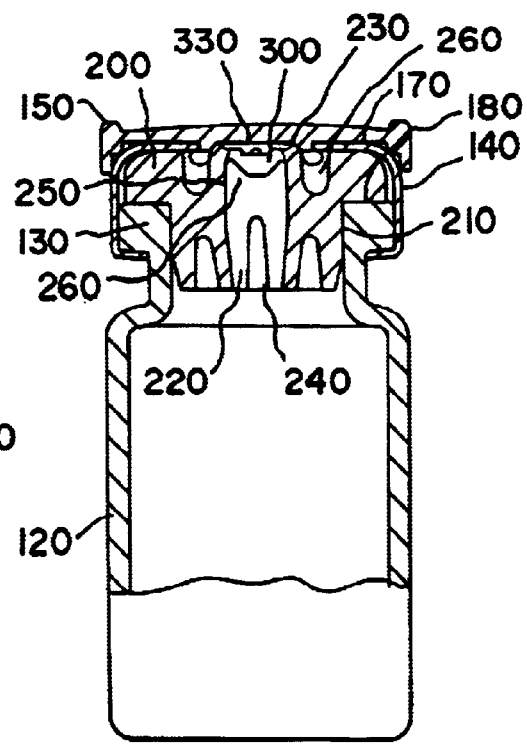
FIG. 5C is a partial sectional view of the stoppered medicinal container of FIG. 5A.

As shown in FIG. 5A, the alternative medicinal container 100 includes a bottle 120 with a top mouth portion 130 encircled by a flange 140 and sealed by a cover 150 that is instructed in FIG. 5B to be "flipped up" at a corner 160 and torn to expose the flange rim 170 of FIG. 5C, which shows the stopper 200 in snug fit within mouth portion 130 of the bottle 120. The stopper 200 may include a rib 210, or the like, to improve the seal. The flange 140 overlies the top edge 180 of bottle 120.

The stopper 200 may be of an elastomeric, rubber-like material or a hard, self-lubricating plastic such as TEFLON M material. The stopper 200 has a throughbore 220 which extends form an entry portion 230 to an exit portion or opening 240.

Aligned with the entry portion 230 of the stopper 200 is the outer surface 330 of the plug 300. Surrounding the plug 300 is a neck 250 of the stopper 200 to which the stopper 200 is frangibly connected. In FIG. 5C the neck 250 is surrounded by a recess 260 below the entry position 230.

As more clearly shown in FIGS. 6C and 6E, the bore 220 of the stopper 200 has side channels 280-1 and 280-2 in the side wall 290, as shown in FIG. 6E.

Details of the plug 300 are shown in FIGS. 6C and 6F. The plug 300 has an upper surface 310 with protrusions 320-1 though 320-4 in order to space the tip of an inserted fitment, as discussed below, from the surface 310 in order to allow fluid flow from the fitment to the surface 310. The plug 300 is attached to the stopper 200 by a circumferential frangible connection 311. As shown in FIG. 7A, which is an enlarged, partial sectional view of the container of FIG. 5C, after removal of the cap 150, a Luer fitment in the form of a syringe 400 has its tip 410 brought near the surface 310 of the plug 300, preparatory to activation.

The syringe 400 has its blunt tubular leading end tip 410 surrounded by a Luer threaded housing 420, includes a plunger (not shown) and is calibrated with indicia which permit a proper dosage of medication to be withdrawn into the barrel 430 of the syringe 400.

As indicated in FIG. 7B, when the tip 410 is brought into contact with the protuberances 320-1 through 320-4, and the housing 420 is pushed into the groove 260, the frangible connection 311 is severed and the plug 300 is depressed into the bore 220, and fluid can be exchanged between the syringe and the container. The flow is through the channels and the bore of the syringe.

In actual practice, blunt end 410 is inserted against the plug 300 and into the bore 210 with the plunger extended. For the withdrawal of fluid, air is injected into the container 100 to pressurize contained fluid and facilitate its withdrawal. The plunger can be drawn out of the barrel 430 of the syringe 400 to the position appropriate for a desired dosage. There is an interference fit between blunt nose end 440 and the bore 220 to effectively grip the syringe in the stopper during medication transfer to minimize spillage.

FIG. 8A is a partial sectional view of the container of FIG. 1C during activation by a cannula 40', while FIG. 8B is a partial sectional view of the container of FIG. 1C during activation by a Luer fitment 40.

FIG. 8C is a partial sectional view of the container of FIG. 5C during activation by a cannula 400', while FIG. 8D is a partial sectional view of the container of FIG. 5C during activation by a Luer fitment 400.

FIG. 9A is an enlarged, partial sectional view of another alternative embodiment of the invention preparatory to activation by a Luer fitment. The three basic components for the needleless transfer of medication between the container 500 and a needleless syringe 40 in FIG. 9A include the syringe 40, a stopper 600 and a plug 700 for the stopper 600.

It is the combination of the stopper 600 and the plug 700 that permits the needleless transfer of medication with reduced danger of pathogen and other contamination.

As shown in FIG. 9A, the medicinal container 500 includes a bottle 512 with a top mouth portion 513 encircled by a flange 514 and sealed by a cover that has been torn away to expose the flange rim 517, with the stopper 600 in snug fit within mouth portion 513 of the bottle 512. The plug 700 in the stopper 600 includes a flange 721, or the like, to fix the position of the plug 700 on the ledge 621 of the stopper 600.

The stopper 600 may be of an elastomeric, rubber-like material or a hard, self-lubricating plastic such as TEFLON Material material. The stopper 600 has a throughbore 622 which extends from an entry portion to an exit portion or opening.

Aligned with the entry portion of the stopper 600 is the outer surface 731 of the plug 700. Surrounding the plug 700 is a neck 625 of the stopper 600. The neck 625 is surrounded by a recess 626 below the entry position. The neck 625 can have Leur threads (not shown).

The bore 622 of the stopper 600 has side channels 627-1 and 627-2, and the side wall 629 is connected from side-to side with outlets 628-1 through 628-4 as shown in FIG. 9C.

The plug 700 has an upper surface 731 with protrusions 732-1 though 732-4 in order to space the tip of an inserted fitment, as discussed below, from the surface 731 in order to allow fluid flow from the fitment to the surface 731. The plug 700 also has lateral ledge 721 in the side wall 734.

As shown in FIG. 9B, which is a sectional view of the container 500 after cap removal, a Luer fitment in the form of a syringe 40 has its tip 41 brought near the surface 731 of the plug 700, preparatory to activation.

The syringe 40 has its blunt tubular leading end tip 41 surrounded by a Luer threaded housing 42, includes a plunger (not shown) and is calibrated with indicia which permit a proper dosage of medication to be withdrawn into the barrel 43 of the syringe 40.

As indicated in FIG. 9B, when the tip 41 is brought into contact with the protuberances 732-1 through 732-4, and the housing 42 is pushed into the groove 626, the plug 700 is depressed into the bore 622 and fluid can be exchanged between the syringe and the container. The flow is through the channels and the bore of the syringe.

In actual practice, blunt end 41 is inserted against the plug 700 and into the bore with the plunger extended. For the withdrawal of fluid, air is injected into the container 500 to pressurize contained fluid and facilitate its withdrawal. The plunger can be drawn out of the barrel 43 of the syringe 40 to the position appropriate for a desired dosage. There is an interference fit between blunt nose end 44 and the bore 622 to effectively grip the syringe in the stopper during medication transfer to minimize spillage.

As the nose end 44 is pushed into the bore 622 the flange 721 becomes disengaged from the ledge 621, and the plug is retained by the elastically expanded side wall 629. When the nose end 44 is withdrawn, the plug 700 returns to the configuration of FIG. 9A.

FIG. 10A is an enlarged, partial sectional view of a further alternative embodiment of the invention preparatory to activation by a Luer fitment. Again, the three basic Id components for the needleless transfer of medication between the container 1000 and a needleless syringe 40 in FIG. 9A include the syringe 40, a stopper 1600 and a plug 1700 for the stopper 1600.

It is the combination of the stopper 1600 and the plug 1700 that permits the needleless transfer of medication with reduced danger of pathogen and other contamination.

As shown in FIG. 10A, the medicinal container 1000 includes a bottle 1512 with a top mouth portion 1513 encircled by a flange 1514 and sealed by a cover that is torn away to expose the flange rim 1517, with the stopper 1600 in snug fit within mouth portion 1513 of the bottle 1512. T he plug 1700 in the stopper 1600 includes an intermediate rim 1721, or the like, to fix the position of the plug 1700 against the indent 1621 of the stopper 1600.

The stopper 1600 has a throughbore 1622 which extends from an entry portion to an exit portion or opening. Aligned with the entry portion of the stopper 1600 is the outer surface 1731 of the plug 1700. Surrounding the plug 1700 is a neck 1625 of the stopper 1600. The neck 1625 is surrounded by a recess 1626 below the entry position. The neck 1625 can have Leur threads (not shown).

The side wall 1629 is connected from side-to side with outlets 1628-1 through 1628-4 as shown in FIG. 9C.

The plug 1700 has an upper surface 1731 with protrusions, of which protrusions 1732-1 though 1732-3 are visible in FIGS. 10A and 10B in order to space the tip of an inserted fitment, as discussed below, from the surface 1731 in order to allow fluid flow from the fitment to the surface 1731.

As indicated in FIG. 10B, when the tip 41 is brought into contact with the protuberances 1732-1 through 1732-4, and the housing 42 is pushed into the groove 1626, the plug 1700 is depressed into the bore 1622, creating side channels 1627-1 and 1627-2, and and fluid can be exchanged between the syringe and the container. The flow is through the channels and the bore of the syringe.

As the nose end 44 is pushed into the bore 1622 the flange 1721 becomes disengaged from the ledge 1621, and the plug is retained by the elastically expanded side wall 1629. When the nose end 44 is withdrawn, the plug 1700 returns to the configuration of FIG. 11A.

Various changes, alternatives and modifications will become apparent to a person of ordinary skill in the art following a reading of the foregoing specification. It is intended that all such changes, alternatives and modifications as fall within the scope of the appended claims be considered part of the present invention.

What is claimed:

1. The method of accessing a port, comprising the steps of:
   (a) swabbing a movable plug positioned flush with the bore of a stopper, for which said bore extends from an entry position, where said plug is swabbed, to an exit position;
   (b) moving said plug within said bore away from said entry position;
   whereby communication can be established along said said bore between said entry position and said exit position.

2. The method of claim 1 for accessing a port, further comprising the step of swabbing an integral surface of said movable plug extending integrally across said bore.

3. The method of claim 1 for accessing a port, further comprising the step of:

swabbing said movable plug with respect to frangible, connections thereof to said bore.

4. The method of claim 1 for accessing a port, further comprising the step of: slidably moving said plug along said bore.

5. The method of claim 1 for accessing a port, further comprising:

engaging said plug by a filament with a transverse gap between a portion of the exterior surface of said plug and the engagement end of said fitment.

6. The method of claim 1 for accessing a port, further comprising: piercing said plug by a cannula.

7. The method of claim 1 for accessing a port, further comprising the step of:

engaging a collar of said stopper at said entry position of said bore.

8. The method of claim 7 for accessing a port, further comprising the step of:

engaging eternal Luer threads of said collar.

9. The method of claim 1 for accessing a port, further comprising the step of:

stretching an apertured membrane that spans said exit position of said bore.

10. The method of claim 1 for accessing a port, further comprising the step of:

causing fluid to flow in an auxiliary channel of said bore when said plug is depressed in said bore.

11. The method of accessing a port, comprising the steps of:

moving a plug to the entry position of a bore extending to an exit position of a port;

and engaging said plug at said entry position and moving said plug through said bore, further including the step of frangibly connecting said plug to said bore.

12. The method of accessing a port, comprising the steps of moving a plug to the entry position of a bore extending to an exit position of a port; and engaging said plug at said entry position and moving said plug through said bore, further including the step of piercing said plug by a cannula with said plug seated in a stopper.

13. A method of transferring fluid from a container, comprising the steps of:

(a) positioning a stopper in a neck portion of a container having a central throughbore extending from an outer surface of said stopper to the interior of said container;

(b) extending a plug into said bore from a position sealed outer surface of said stopper; and (c) depressing said plug to permit fluid to flow between said interior and said outer surface.

14. The method of accessing a port of a container as defined in claim 13 further including the step of extending said plug integrally across said bore to said stopper surrounding said plug.

15. The method of accessing a port of a container as defined in claim 13 further including the step of slidably connecting said plug to said bore.

16. The method of accessing a port of a container as defined in claim 13 further including the step of providing said plug with a non-planar external surface.

17. The method of accessing a port of a container as defined in claim 13 further including the step of spanning said bore with a stretchable membrane.

18. The method of accessing a port of a container as defined in claim 13 further including the step of providing said plug in said stopper with a collar.

19. The method of accessing a port of a container as defined in claim 18 further including the step of providing said collar with external Luer threads.

* * * * *